United States Patent [19]

Wiesenfeldt et al.

[11] Patent Number: 5,206,376

[45] Date of Patent: Apr. 27, 1993

[54] PREPARATION OF 2-AMINO-5-FORMYL-4-HALOTHIAZOLES

[75] Inventors: Matthias Wiesenfeldt, Mutterstadt; Karl-Heinz Etzbach, Frankenthal, both of Fed. Rep. of Germany

[73] Assignee: BASF Aktiengesellschaft, Ludwigshafen, Fed. Rep. of Germany

[21] Appl. No.: 679,200

[22] Filed: Apr. 2, 1991

[30] Foreign Application Priority Data

Apr. 2, 1990 [DE] Fed. Rep. of Germany ....... 4010514

[51] Int. Cl.$^5$ ................. C07D 277/40; C07D 277/593
[52] U.S. Cl. .................... 548/194; 534/795; 534/630
[58] Field of Search ........................ 548/194

[56] References Cited

U.S. PATENT DOCUMENTS 4,395,544 7/1983 Egli ..................................... 548/194
4,505,857 3/1985 Egli ..................................... 548/194

FOREIGN PATENT DOCUMENTS 3015121 11/1980 Fed. Rep. of Germany ...... 548/194
3108077  1/1982 Fed. Rep. of Germany ...... 548/194

OTHER PUBLICATIONS

Ukr. Khim. Zh., vol. 27, pp. 680–681, 1961.
Chemical Abstract, 103: 104522h, pp. 581–582, D. G. Danielyan, et al., "Synthesis of Sulfur-Containing Organic Ligands of the Complexon Type".

Primary Examiner—Floyd D. Higel
Attorney, Agent, or Firm—Oblon, Spivak, McClelland, Maier & Neustadt

[57] ABSTRACT

A process for the preparation of 2-amino-5-formyl-4-halothiazoles by reaction, in a first stage, of thiourea with chloroacetic or bromoacetic acid in the presence of an N,N-disubstituted formamide, followed by treatment of the reaction mixture with a phosphoric trihalide and then with water in the presence of a base.

21 Claims, No Drawings

PREPARATION OF 2-AMINO-5-FORMYL-4-HALOTHIAZOLES

The present invention relates to a novel process for the preparation of 2-amino-5-formyl-4-halothiazoles by reaction, in a first stage, of thiourea with chloroacetic or bromoacetic acid in the presence of an N,N-disubstituted formamide, followed by treatment of the reaction mixture with a phosphoric trihalide and then with water in the presence of a base.

2-Amino-5-formyl-4-halothiazoles are described in DE-A 3,015,121, according to which they can be prepared by reaction of 2-aminothiazolin-4-ones with a Vilsmeier reagent. A drawback of this method is the fact that an intermediate from the thiazoline series must first be prepared and isolated before the Vilsmeier reaction can be carried out therewith.

The preparation of the intermediate 2-aminothiazolin-4-one from chloroacetic acid and thiourea is described, for example, in *Ukr. Khim. Zh.*, Vol. 27, pp. 680 and 681 (1961) or in *Chem. Abstr.*, Vol. 103, 104 544h (1965). The reaction medium used in this method is isobutanol or water.

It is thus an object of the present invention to provide a novel process for the preparation of 2-amino-5-formyl-4-halothiazoles which does not require the use of heterocyclic intermediates and which produces good yields of very pure target products.

We have now found that an advantageous method of preparing 2-amino-5-formyl-4-(chloro or bromo)-thiazole comprises a) reacting, in a first stage, thiourea with chloroacetic or bromoacetic acid in the presence of an N,N-di($C_1$-$C_4$-alkyl)formamide or an N-($C_1$-$C_4$-alkyl)-N-phenylformamide, b) treating the reaction mixture, in a second stage, with phosphorus oxide trichloride or phosphorus oxide tribromide and c) treating the reaction mixture, in a third stage, with water in the presence of a base.

The novel process is preferably used for the preparation of 2-amino-5-formyl-4-chlorothiazole.

Substituted formamides which are suitable for use in the first stage of the process are, for example, N,N-dimethylformamide, N,N-diethylformamide and N-methyl-N-phenylformamide. The use of N,N-dimethylformamide is preferred.

The process of the invention is conveniently carried out by first placing thiourea and substituted formamide in the reactor and adding chloroacetic acid or bromoacetic acid to the said mixture at a temperature of from 0° to 30° C. The molar ratio of thiourea to chloroacetic acid or bromoacetic acid is usually from 1:1 to 1:1.5. The molar ratio of thiourea to substituted formamide is generally from 1:5 to 1:30. The reaction is carried out at a temperature of from 20° to 100° C., preferably from 50° to 90° C. and more preferably from 60° to 85° C.

The process may also be carried out with an inert organic diluent additionally present in the first stage. Suitable inert diluents are, for example, $C_1$-$C_4$-alkyl benzoates such as methyl benzoate and ethyl benzoate, chlorobenzene and nitrobenzene.

Following the reaction, which normally takes from 1 to 3 hours for completion, there is added to the reaction mixture, in the second stage, phosphorus oxide trichloride or phosphorus oxide tribromide at a temperature of from 0° to 40° C., whereupon the reaction is carried out at a temperature of from 50° to 110° C. and preferably from 60° to 90° C.

The use of phosphorus oxide trichloride is preferred.

For each mole of thiourea (first stage) there are generally added form 1 to 5 moles and preferably from 2 to 4 moles and more preferably about 3.5 moles of phosphorus oxide trichloride or phosphorus oxide tribromide.

Following the addition of the phosphorus oxide trihalide, stirring is usually continued for from 3 to 7 hours at the above temperature. The reaction mixture is then treated, in the third stage, with water in the presence of a base.

This is usually effected by adding the reaction mixture to an aqueous solution of a base at a temperature of from 30° to 100° C., preferably from 40° to 80° C. However, temperature control can be optimized in an advantageous manner by adding the reaction mixture to a mixture of base and ice.

Suitable bases are, for example, alkali metal or alkaline earth metal hydroxides such as sodium hydroxide, potassium hydroxide, magnesium hydroxide and calcium hydroxide, pyridine and amines such as triethylamine, tripropylamine, triisopropylamine, tributylamine and N,N-diethylaniline.

The use of alkali metal or alkaline earth metal hydroxides, especially calcium hydroxide, is preferred.

For each mole of thiourea (first stage) there are generally used from 3 to 15 moles and preferably from 4 to 8 moles of base. The concentration of the base in the aqueous solution is usually from 2 to 12% w/w, based on water or ice.

Following the reaction, which normally takes from 1 to 5 hours for completion, the target product is salted out with sodium chloride at a temperature of from 0° to 30° C. If desired, the sodium chloride can be added to the aqueous base solution or to the mixture of base and ice before this is used in the third stage. The precipitated target product is then separated off, washed and dried.

The process of the invention, which may be operated continuously or batchwise, produces very pure 2-amino-5-formyl-4-(chloro or bromo)thiazole in good yields and in a simple manner. The distinctive advantage of our novel process is that the entire conversion, which comprises a number of reaction stages, can be effected without isolating the various intermediates, stages 1 and 2 being carried out, if desired, in a single reactor. This gives rise to a higher space-time yield.

2-Amino-5-formyl-4-(chloro or bromo)thiazole is a valuable intermediate in the synthesis of azo dyes, where it can be used as a diazo component, as described in DE-A 3,108,077.

The invention is illustrated below by the following Example.

EXAMPLE 152 g of thiourea and 1.5 liters of N,N-dimethylformamide were placed in a flask, and, at room temperature, 190 g of chloroacetic acid were added, with stirring, which was continued for 2 hours at 75-80° C. The reaction mixture was then cooled to 40° C., and 644 ml of phosphorus oxide trichloride were then added dropwise. Stirring was continued for 30 minutes at 60° C., and the mixture was then heated to 90° C. and stirred at this temperature for 5 hours. The reaction mixture was then stirred into a mixture of 683 g of sodium chloride and 504 g of calcium hydroxide in 5 kg of ice.

On completion of the exothermic reaction, 1 l of water was added and the mixture then stirred for from 3 to 4 hours at 55° C. The solution was then cooled to 0° C., and the resulting precipitate was filtered off under suction, washed until neutral and dried under reduced pressure. There were obtained 246.7 g (76% of theory) of 2-amino-5-formyl-4-chlorothiazole.

We claim:

1. A process for the preparation of 2-amino-5-formyl-4-(chloro or bromo)thiazole, comprising
   a) reacting, in a first stage, thiourea with chloroacetic or bromoacetic acid in the presence of a disubstituted formamide selected from the group consisting of an N,N-di($C_1$–$C_4$-alkyl)formamide and an N-($C_1$–$C_4$-alkyl)-N-phenylformamide,
   b) treating the reaction mixture, in a second stage, with phosphorus oxide trichloride or phosphorus oxide tribromide, and
   c) treating the reaction mixture, in a third stage, with water in the presence of a base,
   said reacting in said first stage and said treating in said second stage being conducted in a single reactor.

2. A process as claimed in claim 1, wherein the treatment in the second stage is carried out using phosphorus oxide trichloride.

3. The process of claim 1, wherein said thiourea and said chloroacetic or bromoacetic acid are present in a molar ratio of from 1:1 to 1:1.5, and said substituted formamide is present in a molar ratio of 5:1 to 30:1 with respect to said thiourea.

4. The process of claim 1, wherein said reacting in said first stage is conducted at a temperature of from 20° to 100° C.

5. The reaction of claim 3, wherein said reacting in said first stage is conducted at a temperature of from 50° to 90° C.

6. The process of claim 5, wherein said reacting in said first stage is conducted for a length of time of from 1 to 3 hours.

7. The process of claim 6, wherein said reacting in said first stage is carried out in the presence of an inert organic diluent selected from the group consisting of $C_1$–$C_4$-alkyl benzoates, chlorobenzene and nitrobenzene.

8. The reaction of claim 2, wherein said reacting in said first stage is conducted at a temperature of from 60° to 85° C.

9. The reaction of claim 1, wherein said treating in said second stage is conducted at a temperature of from 50° to 100° C.

10. The process of claim 9, wherein said phosphorus oxide trichloride or said phosphorus oxide tribromide in said second stage is present in an amount of from 1 to 5 moles for each mole of thiourea.

11. The process of claim 10, wherein said treating in said second stage is conducted for a length of time from 3 to 7 hours.

12. The process of claim 11, wherein said phosphorus oxide trihalide is present in an amount of from 2 to 4 moles for each mole of thiourea.

13. The process of claim 2, wherein said treating in said second step is conducted at a temperature of from 60° to 90° C.

14. The process of claim 13, wherein said phosphorus oxide trichloride is present in an amount of about 3.5 moles for each mole of thiourea.

15. The process of claim 1, wherein said base is selected from the group consisting of alkali metal or alkaline earth metal hydroxides, pyridine and tri($C_2$–$C_4$-alkyl)amines and N,N-diethylaniline.

16. The process of claim 15, wherein said base is an alkali metal or alkaline earth metal hydroxide selected from the group consisting of sodium hydroxide, potassium hydroxide, magnesium hydroxide and calcium hydroxide.

17. The process of claim 16, wherein said base is calcium hydroxide.

18. The method of claim 15, wherein said base is present in an amount from 3 to 15 moles for each mole of thiourea.

19. The method of claim 17, wherein said base is present in an amount from 4 to 8 moles for each mole of thiourea.

20. The process of claim 1, wherein said disubstituted formamide is dimethylformamide.

21. The process of claim 1, wherein said treating in said third stage is conducted without isolating an intermediate from said second stage.

* * * * *